(12) United States Patent
Davis et al.

(10) Patent No.: US 12,337,134 B2
(45) Date of Patent: Jun. 24, 2025

(54) HUB COMPONENT FOR VENTED CONNECTOR

(71) Applicant: Avent, Inc., Alpharetta, GA (US)

(72) Inventors: Benjamin M. Davis, Woodstock, GA (US); David A. Doornbos, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 309 days.

(21) Appl. No.: 17/826,508

(22) Filed: May 27, 2022

(65) Prior Publication Data

US 2022/0280766 A1 Sep. 8, 2022

Related U.S. Application Data

(60) Division of application No. 16/132,331, filed on Sep. 14, 2018, now Pat. No. 11,376,409, which is a
(Continued)

(51) Int. Cl.
*A61M 39/10* (2006.01)
*A61J 1/14* (2023.01)
(Continued)

(52) U.S. Cl.
CPC ............ *A61M 39/10* (2013.01); *A61J 1/2055* (2015.05); *A61J 1/2075* (2015.05); *A61J 1/2096* (2013.01);
(Continued)

(58) Field of Classification Search
CPC .. A61M 39/10; A61M 39/1011; A61M 39/20; A61M 2039/1027; A61M 2039/1033; A61M 2039/205; A61M 2202/0482; A61M 2230/208; A61M 2230/432; A61J 5/008; A61J 15/0084;
(Continued)

(56) References Cited

U.S. PATENT DOCUMENTS 2,872,060 A 2/1959 Brune et al.
3,057,502 A 10/1962 Wood
(Continued)

FOREIGN PATENT DOCUMENTS

CA 2167572 A1 2/1995
CA 2379187 A1 2/2001
(Continued)

OTHER PUBLICATIONS

International Application No. PCT/US2018/051248, International Search Report and Written Opinion mailed on Mar. 13, 2019, 11 pages.
(Continued)

*Primary Examiner* — Lauren P Farrar
(74) *Attorney, Agent, or Firm* — Meunier Carlin & Curfman LLC

(57) ABSTRACT

A hub component for a vented connector including a generally elongate cylindrical body having a first end and a second end. The first end of the hub component includes one or more fingers or clips for engagement with one or more vents of the vented connector. The second end of the hub component can be configured for compatible engagement with a carbon dioxide detector.

13 Claims, 8 Drawing Sheets

Related U.S. Application Data continuation-in-part of application No. 14/844,956, filed on Sep. 3, 2015, now Pat. No. 10,668,263.

(60) Provisional application No. 62/559,006, filed on Sep. 15, 2017, provisional application No. 62/192,614, filed on Jul. 15, 2015, provisional application No. 62/047,389, filed on Sep. 8, 2014.

(51) Int. Cl.
   *A61J 1/20*   (2006.01)
   *A61J 15/00*  (2006.01)
   *A61M 39/20*  (2006.01)

(52) U.S. Cl.
   CPC ......... *A61J 15/008* (2015.05); *A61J 15/0084* (2015.05); *A61J 15/0096* (2013.01); *A61M 39/1011* (2013.01); *A61M 39/20* (2013.01); *A61J 1/1425* (2015.05); *A61J 1/1481* (2015.05); *A61J 2200/70* (2013.01); *A61M 2039/1027* (2013.01); *A61M 2039/1033* (2013.01); *A61M 2039/205* (2013.01); *A61M 2202/0482* (2013.01); *A61M 2230/208* (2013.01); *A61M 2230/432* (2013.01)

(58) Field of Classification Search
   CPC .... A61J 15/0096; A61J 1/2075; A61J 1/2096; A61J 2200/70
   See application file for complete search history.

(56) References Cited

U.S. PATENT DOCUMENTS

| | | |
|---|---|---|
| 3,307,552 A | 3/1967 | Strawn |
| 3,339,772 A | 9/1967 | Miller |
| 3,716,163 A | 2/1973 | Marcel |
| 4,214,586 A | 7/1980 | Mericle |
| 4,230,231 A | 10/1980 | Burnett et al. |
| 4,237,935 A | 12/1980 | Demonte et al. |
| 4,349,024 A | 9/1982 | Ralston, Jr. |
| 4,416,273 A | 11/1983 | Grimes |
| 4,417,890 A | 11/1983 | Dennehey et al. |
| 4,573,602 A | 3/1986 | Goldberg |
| 4,597,758 A | 6/1986 | Aalto et al. |
| 4,904,238 A | 2/1990 | Williams |
| 4,963,132 A | 10/1990 | Gibson |
| 4,994,068 A | 2/1991 | Hufnagle |
| 5,184,742 A | 2/1993 | DeCaprio et al. |
| 5,385,372 A | 1/1995 | Utterberg |
| 5,401,255 A | 3/1995 | Sutherland et al. |
| 5,591,344 A | 1/1997 | Kenley et al. |
| 5,782,808 A | 7/1998 | Folden |
| 5,813,554 A | 9/1998 | Marangoni Graziani et al. |
| 5,830,195 A | 11/1998 | Peters et al. |
| 5,857,580 A | 1/1999 | Iidaka |
| 5,881,774 A | 3/1999 | Utterberg |
| 5,951,519 A | 9/1999 | Utterberg |
| 6,183,465 B1 | 2/2001 | Meier et al. |
| D463,546 S | 9/2002 | Jansen et al. |
| 6,447,480 B1 | 9/2002 | Brunel |
| D473,646 S | 4/2003 | Baillargeon et al. |
| 6,632,199 B1 | 10/2003 | Tucker et al. |
| 6,808,521 B1 | 10/2004 | McMichael |
| 6,883,778 B1 | 4/2005 | Newton et al. |
| 7,077,829 B2 | 7/2006 | McGuckin, Jr. et al. |
| 7,080,672 B2 | 7/2006 | Fournie et al. |
| 7,578,803 B2 | 8/2009 | Rome et al. |
| 7,628,782 B2 | 12/2009 | Adair et al. |
| 7,658,734 B2 | 2/2010 | Adair et al. |
| 7,686,823 B2 | 3/2010 | Pingleton et al. |
| 7,988,683 B2 | 8/2011 | Adair et al. |
| 8,066,670 B2 | 11/2011 | Cluff et al. |
| D665,497 S | 8/2012 | Marshall et al. |
| 8,333,693 B2 | 12/2012 | Hamazaki |
| 8,491,535 B2 | 7/2013 | Limaye |
| 8,506,549 B2 | 8/2013 | Breuer-Thal et al. |
| 8,652,104 B2 | 2/2014 | Goral et al. |
| 8,852,168 B2 | 10/2014 | Barron et al. |
| 8,915,883 B2 | 12/2014 | Baid |
| 8,932,264 B2 | 1/2015 | DeSalvo |
| D736,906 S | 8/2015 | Schultz |
| D737,436 S | 8/2015 | Lev et al. |
| 9,308,362 B2 | 4/2016 | Mansour et al. |
| 9,399,116 B2 | 7/2016 | Goral et al. |
| 9,579,452 B2 | 2/2017 | Adair et al. |
| 9,604,046 B2 | 3/2017 | Steele |
| 9,814,871 B2 | 11/2017 | Wlodarczyk et al. |
| 9,895,526 B2 | 2/2018 | Korogi et al. |
| 10,420,709 B2 | 9/2019 | Davis et al. |
| 2002/0173748 A1 | 11/2002 | McConnell et al. |
| 2003/0032940 A1 | 2/2003 | Doyle |
| 2004/0168690 A1 | 9/2004 | Payne |
| 2004/0211484 A1* | 10/2004 | Fournie .................. A61J 1/10 |
| | | 141/329 |
| 2004/0238776 A1 | 12/2004 | Peters et al. |
| 2005/0124935 A1 | 6/2005 | McMichael |
| 2005/0261664 A1 | 11/2005 | Rome et al. |
| 2006/0060202 A1 | 3/2006 | Flynn et al. |
| 2006/0161115 A1 | 7/2006 | Fangrow |
| 2008/0103486 A1 | 5/2008 | Owens |
| 2008/0128646 A1 | 6/2008 | Clawson |
| 2008/0183153 A1 | 7/2008 | Enns |
| 2008/0200904 A1 | 8/2008 | Cluff et al. |
| 2009/0182309 A1 | 7/2009 | Muffly |
| 2010/0292673 A1 | 11/2010 | Korogi et al. |
| 2011/0044850 A1 | 2/2011 | Solomon et al. |
| 2011/0144481 A1 | 6/2011 | Feer et al. |
| 2011/0240162 A1 | 10/2011 | Zeyfang |
| 2011/0270230 A1 | 11/2011 | Sage et al. |
| 2012/0022457 A1 | 1/2012 | Silver |
| 2012/0029481 A1 | 2/2012 | Pech et al. |
| 2012/0041426 A1* | 2/2012 | Bizup ............... A61M 39/1011 |
| | | 604/536 |
| 2012/0191029 A1 | 7/2012 | Hopf et al. |
| 2012/0302997 A1 | 11/2012 | Gardner et al. |
| 2012/0323221 A1 | 12/2012 | Gallo et al. |
| 2013/0079730 A1 | 3/2013 | Mosler et al. |
| 2013/0103002 A1 | 4/2013 | Fruenlund et al. |
| 2014/0261758 A1 | 9/2014 | Wlodarczyk et al. |
| 2014/0276458 A1 | 9/2014 | Mansour et al. |
| 2014/0276652 A1* | 9/2014 | Gittard ............... A61M 39/1011 |
| | | 604/536 |
| 2015/0005716 A1 | 1/2015 | Adair et al. |
| 2015/0297839 A1 | 10/2015 | Sanders et al. |
| 2016/0067471 A1 | 3/2016 | Ingram et al. |
| 2016/0089528 A1 | 3/2016 | Schuessler |
| 2016/0151584 A1 | 6/2016 | Deleuil |
| 2016/0206516 A1 | 7/2016 | Kunishige et al. |
| 2016/0296724 A1 | 10/2016 | Goral et al. |
| 2016/0317393 A1 | 11/2016 | Davis et al. |
| 2018/0071169 A1 | 3/2018 | Davis et al. |

FOREIGN PATENT DOCUMENTS

| | | |
|---|---|---|
| EP | 0 453 264 A1 | 10/1991 |
| EP | 2 583 715 A1 | 4/2013 |
| GB | 2 453 361 A | 4/2009 |
| JP | A09000618 | 9/1997 |
| JP | 2008518719 A | 6/2008 |
| WO | WO 99/64103 A1 | 12/1999 |
| WO | WO 2006/052655 A2 | 5/2006 |
| WO | 2011/066586 | 6/2011 |

OTHER PUBLICATIONS

Canadian Examiner's Report for Application CA2,959,393, dated Jun. 4, 2018.
English Translation of Japanese Office Action for JP Ap. No. 2017-531979; Mar. 27, 2018; 4pgs.
International Search Report & Written Opinion for PCT/US2015/048382; Nov. 5, 2015; 11 pgs.

(56) References Cited

OTHER PUBLICATIONS

ISO 80369-3, Small Bore Enteral Connector Standards; 3 pgs; Jul. 21, 2014.
New ISO Tubing Connector Standards: A Follow-Up to the Sentinel Event Alert Webinar PowerPoint Presentation: www.jointcommission.org: 50 pgs; Dec. 3, 2014.
New Tube Feeding Connectors Webinar PowerPoint Presentation; www.oley.org; 24 pgs; Jun. 24, 2014.

\* cited by examiner

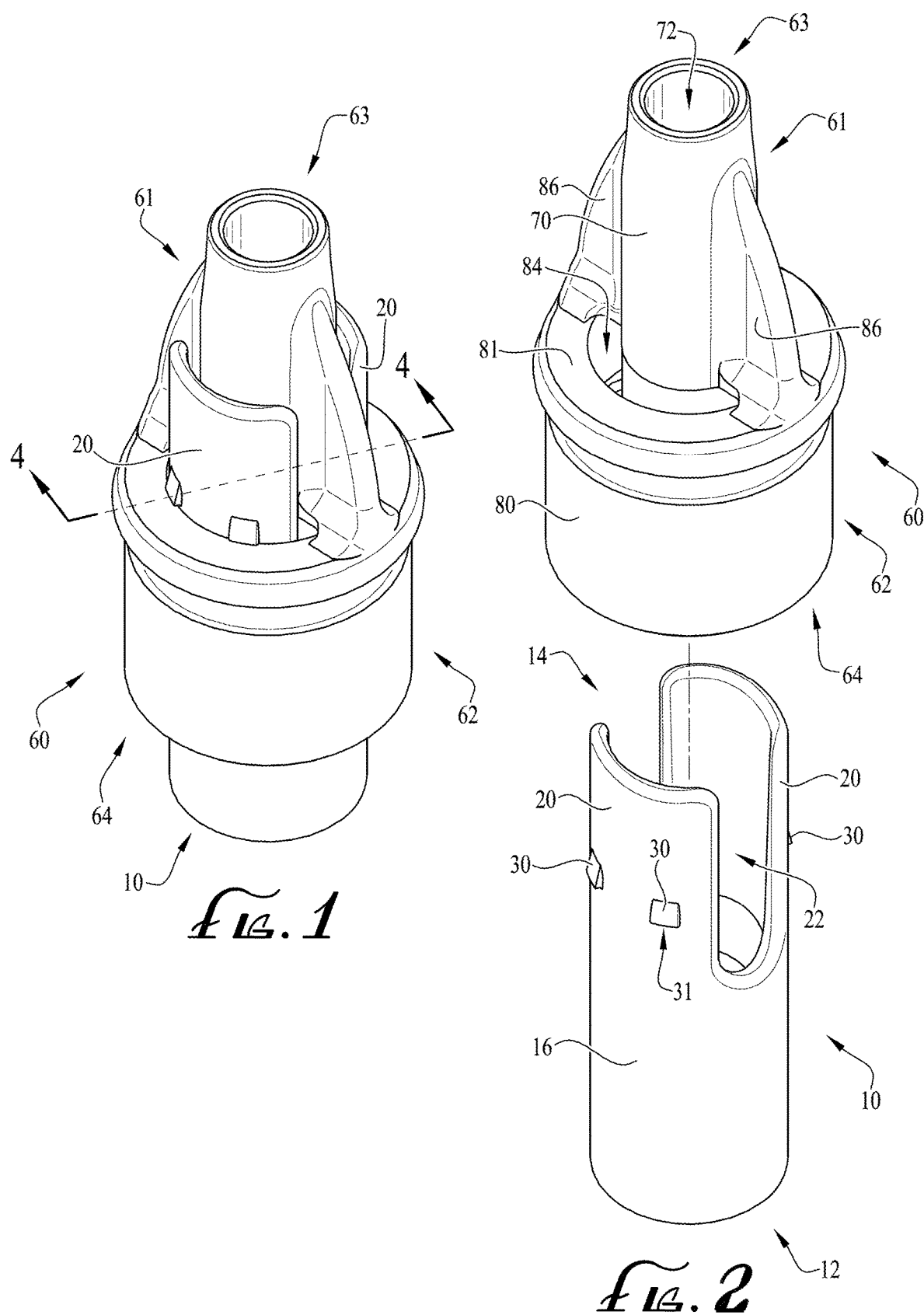

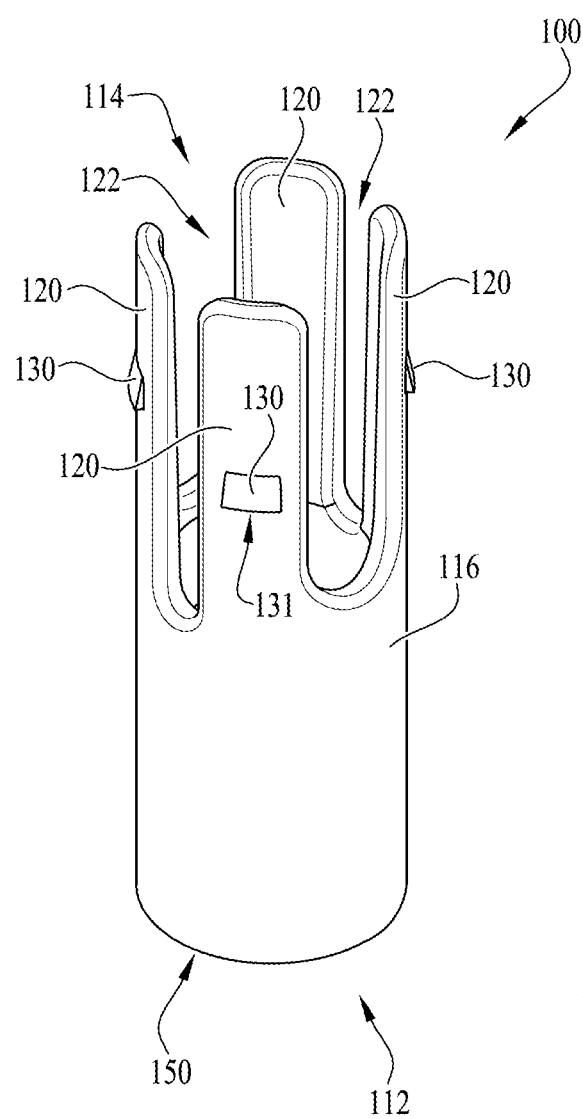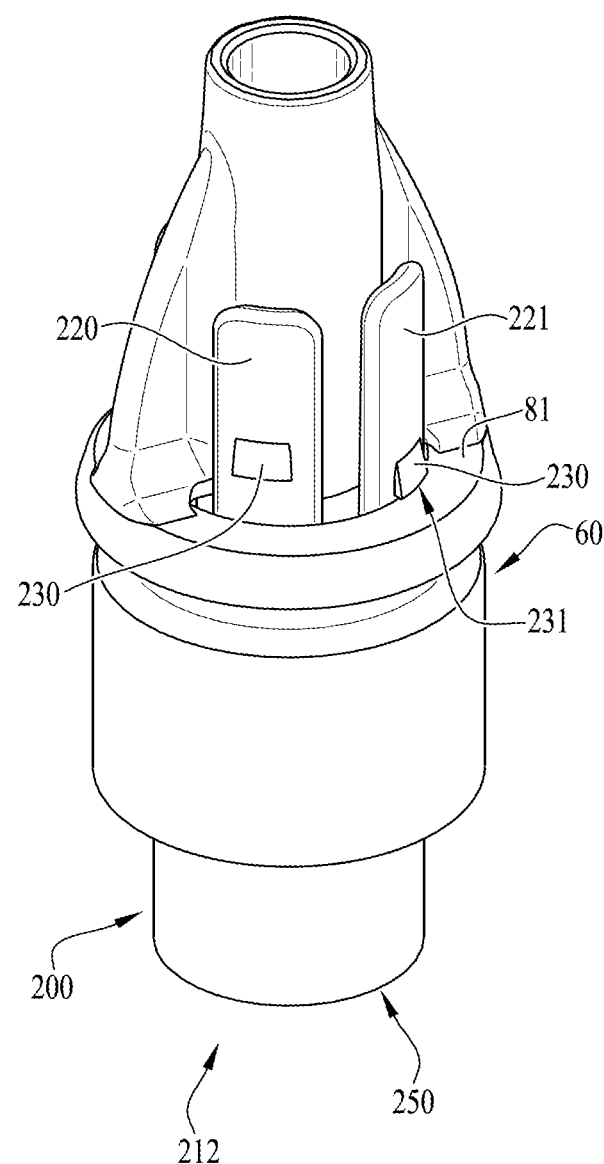

HUB COMPONENT FOR VENTED CONNECTOR

CROSS-REFERENCE TO RELATED APPLICATION

This application is a divisional application of U.S. patent application Ser. No. 16/132,331 filed Sep. 14, 2018, which claims priority benefit of U.S. Provisional Patent Application Ser. No. 62/559,006 filed Sep. 15, 2017, and is a continuation-in-part of U.S. Non-Provisional patent application Ser. No. 14/844,956 filed Sep. 3, 2015, now U.S. Pat. No. 10,668,263 granted on Jun. 2, 2020, which claims the priority benefit of U.S. Provisional Patent Application Ser. No. 62/047,389 filed Sep. 8, 2014, and U.S. Provisional Patent Application Ser. No. 62/192,614 filed Jul. 15, 2015, the entireties of which are hereby incorporated herein by reference for all purposes.

TECHNICAL FIELD

The present invention relates generally to medical devices, and more particularly to connectors and couplings and other components for vessels for fluids in the medical field.

SUMMARY OF THE INVENTION

In example embodiments, the present invention relates to a hub component for connection with a vented connector.

In one aspect, the invention relates to a hub component including a generally elongate body, a coupling portion formed at the first end, one or more elongate fingers formed at the second end, and a receiver defined within a portion of the body between the first and second ends. In example embodiments, the elongate body has a first end and a second end defining a length therebetween, and a lumen extending through the body from the first end to the second end.

In example embodiments, an outer surface of the one or more fingers include at least one engagement member formed thereon. In example embodiments, the receiver is configured for coupling complementary engagement with a connector-receiving portion of a connector. In example embodiments, the connector-receiving portion includes a male hub. In example embodiments, the male hub includes a male ISO 80369-3 compatible coupling and the receiver includes a female ISO 80369-3 compatible coupling. In example embodiments, the connector-receiving portion further includes an outer cylindrical collar surrounding the male hub and defines an annular space therebetween, the outer cylindrical collar having an endwall defining one or more vents, wherein the one or more fingers are configured for extension through the one or more vents when the receiver is connected with the male hub. In example embodiments, an outer surface of the one or more fingers include an engagement member configured for engagement with the endwall of the collar when the male hub is connected with the receiver of the elongate body. In example embodiments, the one or more fingers include a pair of opposing fingers defining a pair of elongate channels therebetween. In example embodiments, the one or more fingers include a circular array of four space-apart fingers, wherein at least one of the four fingers comprises an engagement member extending from an outer surface thereof. In example embodiments, a first pair of fingers and a second pair of fingers, the first pair of fingers including at least one engagement member formed on an outer surface thereof at a first height and the second pair of fingers comprising at least one engagement member formed on an outer surface thereof at a second height, wherein the first height is not identical to the second height.

In example embodiments, the length of the elongate body is between about 5-200 millimeters. In example embodiments, the hub component further includes a lumen extension tip formed with the receiver. In example embodiments, the coupling portion is configured for connection with a sensor or detector. In example embodiments, the sensor or detector can be a carbon dioxide detector, a pH indicator or other sensor or detector so as to ensure proper gastric placement of a feeding tube.

In another aspect, the invention relates to a component for coupling engagement with a vented connector. In example embodiments, the vented connector includes a body having a lumen extending therethrough and defining a vessel-attaching portion and a component-attaching portion, the component-attaching portion including a cylindrical collar surrounding the body and having an endwall having one or more vents. The component includes a cylindrical body, a coupling portion defined at the first end, at least one clip or finger defined at the second end, and a receiver formed within the cylindrical body between the first and second ends. In example embodiments, the at least one clip or finger is configured for passing through the one or more vents so as to permit the body of component-attaching portion to engage with the receiver. In example embodiments, the cylindrical body extends from a first end to a generally opposite second end, and a lumen extends through the body from the first end to the second end.

In example embodiments, the body of the component-attaching portion comprises a male hub, the male hub being formatted to be compatible with the ISO 80369-3 design standard, and wherein the receiver is formatted to be compatible with the ISO 80369-3 design standard so as to provide complementary interengagement between the component and the vented connector. In example embodiments, an outer surface of the at least one clip or finger comprises an engagement member having an engagement surface, the engagement surface configured for interfering with the endwall of the cylindrical collar when the receiver is connected with the body of the component-attaching portion. In example embodiments, the second end of the cylindrical body includes at least two fingers, wherein one of the at least two fingers includes an engagement member formed on an outer surface thereof and positioned at a first height and wherein the other of the at least two fingers includes an engagement member formed on an outer surface thereof and positioned at a second height. In example embodiments, the component can be configured for connecting with the vented connector in either of a vented configuration or a sealed configuration, wherein in the vented configuration the engagement member positioned at the first height is engaged with the endwall so as to provide at least some space between an inner surface of the receiver and an outer surface of the body of the vented connector, and wherein in the sealed configuration the engagement member positioned at the second height is engaged with the endwall so as to provide a sealed, interference fit between the inner surface of the receiver and an outer surface of the body of the vented connector.

In yet another aspect, the invention relates to a component for coupling engagement with nutritional or medicinal fluid transfer systems or components. In example embodiments, the component includes an elongate body extending between a first end and a second end and defining a lumen extending therethrough. The first end includes a coupling portion and the second end includes one or more fingers. A receiver is formed in the elongate body between the first and second ends, wherein the receiver includes an inner surface for compatible engagement with a male hub.

In example embodiments, the coupling portion of the second end is configured for coupling engagement with another medical device, component, vessel, detector or sensor. In example embodiments, the detector is capable of determining the presence of carbon dioxide and/or measuring the acidity of a fluid.

BRIEF DESCRIPTION OF THE DRAWINGS

FIG. 1 shows a perspective view of a hub component according to an example embodiment of the present invention, the hub component connected with a known vented connector for medical fluid vessels.

FIG. 2 shows a perspective assembly view of the hub component of FIG. 1, wherein the hub component and the vented connector are disassembled and spaced apart from each other.

FIG. 5 shows a perspective view of a hub component according to another example embodiment of the present invention.

FIG. 6 shows a perspective view of a hub component according to another example embodiment of the present invention, showing the hub component connected with a known vented connector for medical fluid vessels.

DETAILED DESCRIPTION OF EXAMPLE EMBODIMENTS

Figure 3:
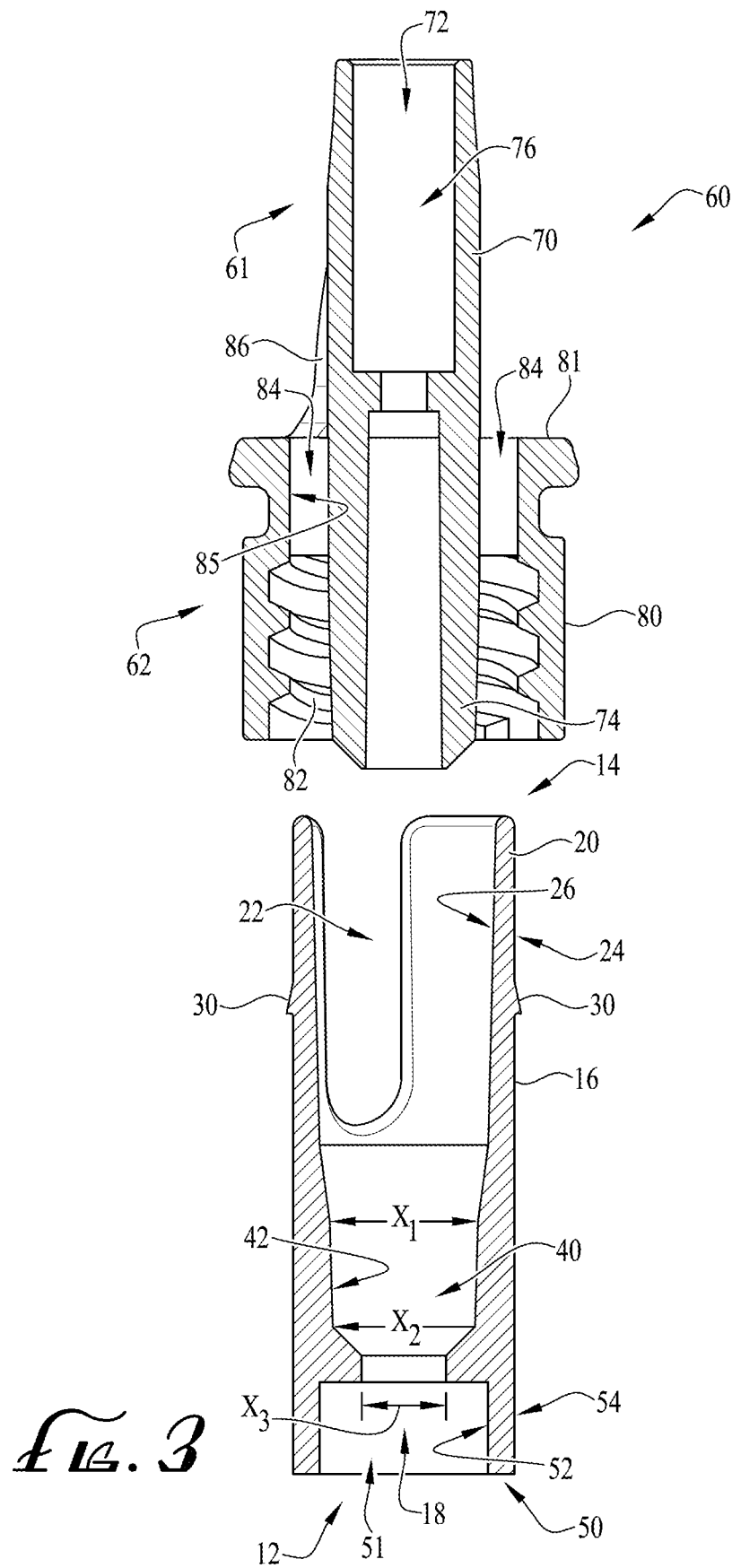
FIG. 3 shows a cross-sectional view of the disassembled hub component and vented connector of FIG. 2.

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-2 show a hub connector or component 10 according to an example embodiment of the present invention. In the depicted example, the component 10 is configured for connecting with a connector 60. For example, according to example embodiments, the connector 60 comprises a vessel-attaching portion 61 defining a rear end 63, a coupling-attaching portion 62 defining a front end 64, and a central member or conduit 70 defining a lumen 72 extending longitudinally therethrough from end to end. The vessel-attaching portion 61 attaches to (e.g., receives and secures) the vessel and secures it in place with a good seal by conventional structures such as crimps or adhesives so that the vessel extends longitudinally from the rear end. In example embodiments, the vessel is generally a tube, though the term "vessel" is intended to be broadly construed to include any carrier or container for a fluid as well as any fluid-delivery device, and as such in other embodiments the vessel is a catheter, hose, feeding tube, bottle, bag, syringe, pump, or the like. According to one example embodiment, the vessel-attaching portion 61 defines a receiver or connecting portion 76 (that is configured for receiving a feeding tube or the like). In other example embodiments, the connecting portion 76 can be configured as desired, for example, such that a vessel can be permanently coupled therewith. In some example embodiments, the vessel can optionally be removably coupled therewith.

In example embodiments, the component 10 of the present invention is configured for connection with the coupling-attaching portion 62 of the connector 60. According to example embodiments, the coupling-attaching portion 62 comprises a male hub 74 (comprising the lumen 72 extending therethrough), and a cylindrical collar 80 extending around the entirety thereof and comprising threads 82 formed on an inside or interior surface thereof. In example embodiments, the connector 60 is vented to provide for fluid drainage and airflow ventilation. For example, an endwall 81 of the cylindrical collar 80 of the connector 60 comprises at least one vent opening 84 (e.g., two, as depicted) providing fluid communication between an annular space defined generally near the coupling-attaching portion (e.g., between an interior surface of the collar 80 and an outer surface of the male hub 74) and external to the annular space. U.S. Published Patent Application US 2016/0067471, Ser. No. 14/844,956 is incorporated herein by reference in its entirety and discloses a vented connector comprising a vessel-attaching portion defining a rear end, a coupling-attaching portion defining a front end, a lumen extending longitudinally therethrough from end to end, and at least one vent opening. According to example embodiments, two connecting portions 86 (depicted as spokes) fix together the conduit 70 (and male hub 74) with the cylindrical collar 80 so as to axially align the conduit 70 with the cylindrical collar 80.

According to example embodiments, the component 10 is configured for engagement with the coupling-attaching portion 62 of the connector 60. According to some example embodiments, the component 10 is configured for providing an interference fit with the male hub 74. As depicted in FIGS. 1-4, the component 10 comprises a generally cylindrical body 16 extending between a first end 12 and a second end 14 (defining a length L therebetween), and defines a lumen 18 extending entirely through the body 16 from end to end. In example embodiments, the second end 14 comprises at least one elongate member or finger 20 and the first end 12 comprises a coupling 50 (as will be described below). As depicted in FIG. 4, the length L of the component 10 is between about 12-35 millimeters, for example, between about 20-30 millimeters according to one example embodiment, and for example, between about 23-26 millimeters according to another example embodiment. In alternate example embodiments, the length L can be chosen as desired, for example, between about 5-200 millimeters.

According to the depicted embodiment, the second end of the cylindrical body 16 comprises a pair of opposing radial clips or fingers 20 comprising a slot or channel 22 defined between the sides of the fingers 20. In example embodiments, the fingers 20 are configured for passing through a pair of vents 84 formed in the endwall 81 of the coupling-attaching portion 62 of the connector 60, for example, wherein one or more outer protrusions or engagement members 30 pass beyond the endwall 81 so as to provide engagement with the same. In example embodiments, the fingers 20 are generally sized and shaped to extend through the pair of vents 84, for example, which are generally in the form of curved slots. Thus, according to example embodiments, the pair of fingers 20 comprise a cross-section that is shaped to pass through the curved slots. In alternate example embodiments, the fingers can comprise a desired cross-section, and for example, the cross-section of the fingers can be sized and shaped to generally fit within the shape of the vents 84, for example, in the case that the vents are generally curved or sized and shaped as desired, or for example, wherein one or more vents are shaped to be cylindrical, oval, linear and/or non-linear channels, irregular, or otherwise shaped as desired.

The channels 22 that are defined between the fingers 20 are preferably sized and shaped so as to receive the connecting portions 86 when the fingers 20 extend through the vents 84. In some example embodiments, the channels 22 are generally linear and rectangular in shape, and comprising a curved or radiused lower portion. In other example embodiments, the channels 22 can preferably be shaped and sized as desired, for example, such that they are capable of receiving the connecting portions 86. According to one example embodiment, the channels can be generally non-linear or substantially helical so as to define one or more helical fingers. Thus, according to example embodiments, rather than the fingers being generally linear (and linear channels), the fingers and the channels are generally helical.

Figure 4:
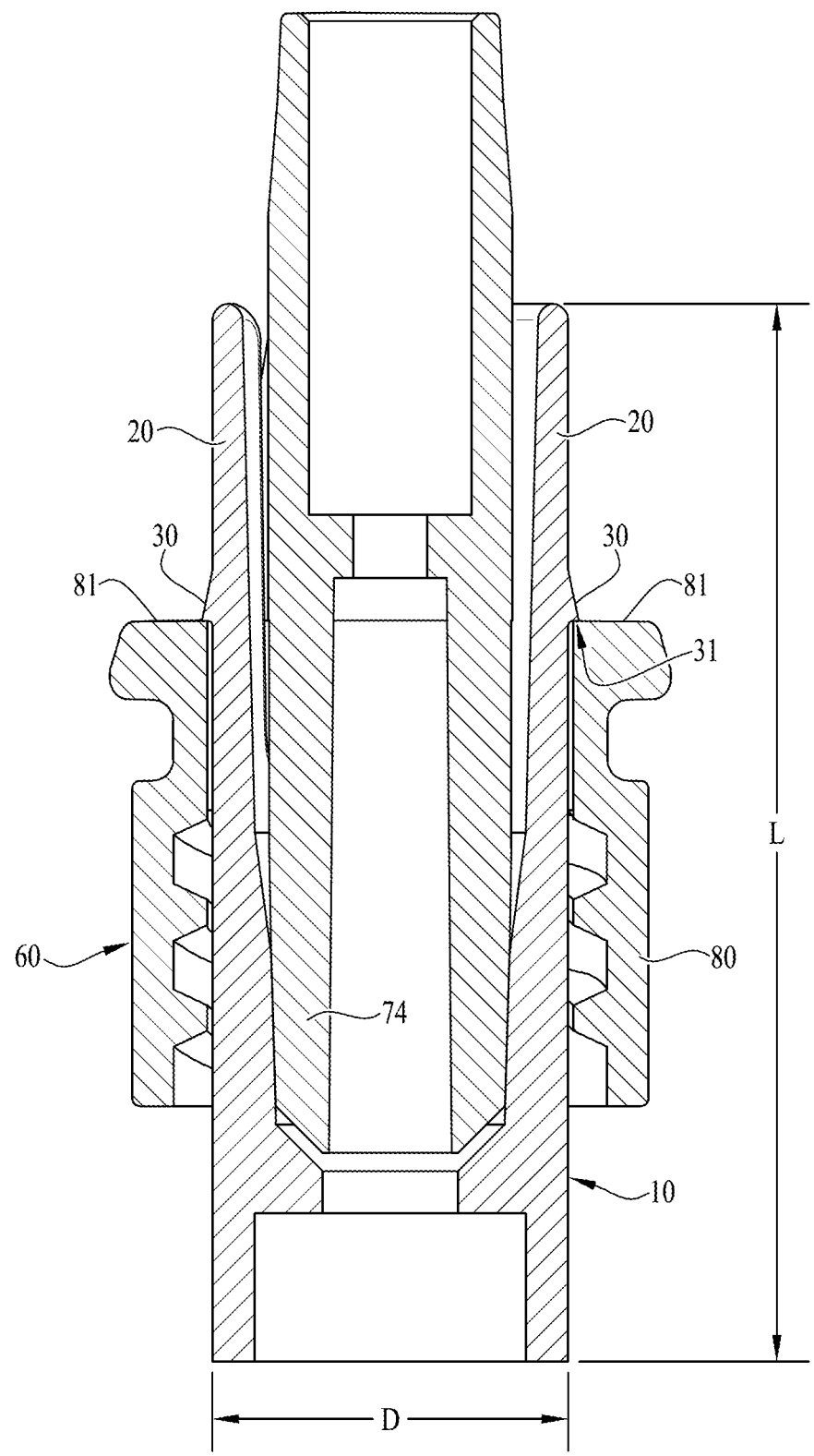
FIG. 4 shows a cross-sectional view of the hub component connected with the vented connector of FIG. 1 taken along line 4-4.

According to example embodiments and as depicted in FIGS. 3-4, an external surface 24 of the fingers 20 comprise the engagement members 30 defined thereon, which are generally sized and shaped to permit the assembly and engagement thereof, however, disconnecting the component 10 from the connector 60 is generally prevented until manipulation of the fingers 20. For example, in example embodiments, pressing inwardly on the fingers 20 (displacing the fingers 20 towards the body 70) disengages the engagement members 30 from the endwall 81 such that the fingers 20 (and engagement members 30 extending therefrom) are provided with sufficient clearance to pass through the vents 84, thereby permitting disconnection of the component 10 from the connector 60.

As depicted in FIG. 4, a lower engagement surface 31 of the engagement members 30 engages with the endwall 81 of the connector-attaching portion 60 while a receiver 40 within the body 16 of the component 10 provides for an interference fit with the male hub 74 of the connector-attaching portion 62. In example embodiments, the lower engagement surface 31 of the engagement members 30 extends outwardly from an exterior surface 24 of the fingers 20 by about 0.22 millimeters. In example embodiments, the outer surface 24 of the fingers 20 is spaced apart from an outer wall of the vents 84 by about 0.125 millimeters, for example, such that about 0.1 millimeters of interference is defined between the engagement surface 31 and the endwall 81. And an inner surface 26 of the fingers 20 are generally spaced about 0.61 millimeters from an outer surface of the body 70. Thus, according to example embodiments, the fingers comprise about 0.61 millimeters of allowable deflection or displacement so as to allow disengagement of the engagement surface 31 and the endwall 81 to permit full separation of the component 10 from the connector 60. In alternate example embodiments, the extension of the engagement surface, the interference with the endwall 81, spacing relative to the vent wall and the body can preferably be configured as desired, for example, to comprise more or less extension, interference, spacing, etc. According to some example embodiments, the engagement surface 31 and the endwall 81 can comprise between about 0.05-5 millimeters of interference when fully assembled. Optionally, as described above, more or less interference can be provided as desired. For example, according to some example embodiments, the engagement members 30 and the endwall 81 (or other portion of the connector 60) can be configured for providing a permanent connection, for example, such that the component 10 and connector 60 are prevented from separation after being connected together.

Referring back to FIGS. 1-2, the fingers 20 each comprise a pair of spaced-apart engagement members comprising the engagement surface 31. In example embodiments, the engagement members 30 are generally ramped or wedge-shaped, or for example, oriented to project from the outer surface 24 to define the lower engagement surface and an angled surface extending from the engagement surface 31 and back into the outer surface 24. In optional example embodiments, the engagement members 30 can be in the form of one or more protrusions, projections, outwardly-extending members(s), nubs, teeth, or other members or engagement couplings that are configured for coupling engagement with the endwall 81 of the connector. According to other example embodiments, the connector 60 can comprise one or more projections and the engagement members can be in the form of one or more recesses or otherwise receivers for engagement with the projections of the connector 60. According to alternate example embodiments, one or more complementary interengagement features, male/female couplings, protrusions, receivers, stop surfaces, or other engagement features can be provided for providing engagement of the fingers 20 with the connector 60, for example, the fingers with the vents 84. In further alternate example embodiments, the fingers 20 are free from engagement members 30.

According to the depicted example embodiment of FIG. 4, the connector-attaching portion 62 and at least the receiver 40 of the component 10 are formatted to be ISO 80369-3 compatible, or for example, where the male hub 74 comprises a non-luer ENFit male compatible coupling and the receiver 40 comprises a female ENFit compatible coupling. Optionally, in alternate example embodiments, the connector-attaching portion 62 and the male hub 74 can be formatted as desired.

As depicted in FIG. 3, the body 16 comprises an inner surface 26 defined along the fingers 20, and an inner surface 42 is defined along an interior of the receiver 40. In example embodiments, the male hub 74 sealingly engages with the receiver 40 such that a friction-fit connection is provided therebetween. According to example embodiments, the inner surface 42 of the receiver 40 is dimensioned to comprise a first diameter $X_1$, a second diameter $X_2$ that is spaced a distance from the first diameter $X_1$, and a third diameter $X_3$ that is defining the opening size of the lumen 18. According to example embodiments, the first diameter $X_1$ is about 5.6 millimeters, the second diameter $X_2$ is about 5.4 millimeters, and the third diameter $X_3$ is about 3.2 millimeters. According to some example embodiments, the first diameter $X_1$ can be between about 2-10 millimeters, the second diameter $X_2$ can be between about 2-10 millimeters, and the third diameter can be between about 2-10 millimeters. According to the depicted example embodiment, the first diameter $X_1$ is about 5.625 millimeters. In alternate example embodiments, the first, second and third diameters $X_1$, $X_2$ and $X_3$ can preferably be sized as desired. For example, according to most example embodiments, the receiver 40 is configured to provide an interference fit with the male hub 74 of the connector-attaching portion 62. In alternate example embodiments, the receiver 40 can be configured for providing a clearance fit with the male hub 74 such that a minimal amount of interference is provided therebetween. Thus, according to some example embodiments, with substantially minimal interference between the receiver 40 and the male hub 74, a minimal seal or substantially no seal at all is provided therebetween.

In example embodiments, the coupling portion 50 of the first end 12 of the component 10 can be configured for coupling engagement with a plurality of components, or for example, can be configured for housing one or more components and for allowing fluid communication with the one or more components with the lumen 18 (and lumen 72 of the male hub 74 when coupled thereto). In some example embodiments, one or more components can be housed within a portion of the component 10 (and in fluid communication with the lumen 18) while still providing a coupling portion 50, or for example, comprising a connector or other coupling member for receiving one or more other components, connectors, vessels, or other components as desired.

For example, according to one example embodiment, the second end 14 of the component 10 is configured for compatible engagement with a sensor or measuring device, for example, a carbon dioxide ($CO_2$) sensor or detector. For example, with a feeding tube extending from the vessel-attaching portion 61 of the connector 60 for gastric placement within a patient, the receiver 40 is coupled with the male hub 74 and the coupling portion 50 receives a $CO_2$ detector, for example, by engaging an inner and/or outer surface 52, 54 thereof, or for example, by otherwise coupling with the first end 12 of the component 10. According to example embodiments, the coupling portion 50 comprises a receiver 51 defining the inner surface 52, and the outer surface 54 is generally provided on an exterior portion thereof. According to example embodiments, the outer surface 54 of the first end defines a diameter D of about 8.4 millimeters. Optionally, according to alternate example embodiments, the diameter D can be between about 0.25 millimeters to about 35 millimeters, or for example, the diameter D can be chosen as desired. In example embodiments, as described above according to one example form, the $CO_2$ detector (or a portion thereof) can be coupled (and sealingly engaged) with the inner surface 52, the outer surface 54, an end surface between the inner and outer surfaces 52, 54, or can otherwise be sealingly engaged therewith.

In example embodiments, the first end 12 (and coupling portion 50) of the component 10 can be a vessel, a vessel from a tube set from a gravity fed bag, a vessel from a tube set connecting to a syringe, a vessel from a tube set connected to a peristaltic pump, a male ISO 80369-3 compatible connector (e.g., generally similar to male hub 74), a bifurcated med port connector (ISO 80369-3), a male slip fit ISO 80369-3 compatible connector, a funnel connector, a small vessel for residual collection, a port and/or reservoir for venting (gastric decompression), and/or any other desirable connector or coupling including Luer, non-luer, Nutrisafe 2, reverse Luer, neuraxial, ISO 80369-3 female compatible connector, etc. Optionally, according to additional example embodiments, the first end 12 of the component 10 can be configured for coupling to other feeding systems, couplings or other available enteral feeding components or connectors. According to additional example embodiments, the coupling portion 50 can be configured for coupling engagement with one or more sensors, couplings, connectors, vessels, measurement devices, other feeding systems, couplings or other available enteral feeding components or connectors. As described above and according to one example embodiment, a $CO_2$ detector is configured for engagement with the coupling portion 50 to ensure proper gastric placement.

According to another example embodiment, the coupling portion 50 comprises two or more couplings, for example, such that one or more sensors and/or detectors or other components can be in fluid communication with the lumen 18 (and lumen 72 of the connector 60) while permitting fluid transfer through the lumen 18 (and lumen 72) to one of the other couplings. For example, in some example embodiments, the coupling portion 50 comprises a connector or other coupling member for connection with a feeding tube set or other fluid delivery conduit or device, and a separate coupling portion is provided at the first end 12 for connecting with a sensor or detector. According to one example embodiment, the component comprises a pH indicator or strip housed therein, and which is in fluid communication with the lumen of the component 10 and connector 60, for example, such that fluids present within the lumen communicate with the strip. In example embodiments, the pH strip can be utilized to indicate the pH level of a patient's stomach contents, and thus, provide an indication of proper gastric placement of the feeding tube or vessel.

FIG. 5 shows a hub component 100 according to another example embodiment of the present invention. In example embodiments, the component 100 is generally similar to the component 10 as described above, for example, comprising a body 116 extending between a first end 112 and a second end 114, at least one finger 120 at the second end 114, and a coupling portion 150 at the first end 112. In example embodiments, the second end 114 comprises four fingers 120 having a curved or radial cross-section for passing through the vents 84, for example, wherein each of the four fingers 120 each comprise engagement members 130 (defining engagement surfaces 131) for independently providing engagement with the endwall 81 of the connector. The fingers 120 are generally spaced apart to define a circular or radial-like array wherein channels 122 are defined therebetween. In example embodiments, two of the channels 122 are sized for receiving the connecting members 86 of the connector 60. In example embodiments, to disconnect and fully separate the component 100 from the connector 60, all four of the fingers 120 are displaced or flexed inwardly to disengage the engagement surfaces 31 from the endwall 81.

FIG. 6 shows a component 200 connected with the connector 60 according to another example embodiment. In example embodiments, the component 200 is generally similar to the component 100 as described above. According to example embodiments, the component comprises a first pair of fingers 220 and a second pair of fingers 221. In example embodiments, the fingers 220 comprise engagement members 230 protruding therefrom and positioned at a first height, and the fingers 221 comprise engagement members 230 positioned at a second height. In example embodiments, the height difference of the engagement members 230 preferably allows for varying level of engagement with the connector. For example, as depicted in FIG. 6, the engagement members 230 of the second pair of fingers 221 are engaged with the endwall 81 whereby the receiver (not shown) is provided with an interference fit with the male hub 74 of the connector. However, according to another example embodiment, at least some separation of the receiver and male hub can be provided by disengaging the engagement members of the fingers 221 so that the engagement members 230 of the fingers 220 engage the endwall 81. Thus, by providing engagement members 230 of varying height (or distance with respect to the ends of the fingers near the second end), the engagement of the component 200 with the connector 60 can vary. For example, according to one example embodiment, when the engagement members 230 of the fingers 220 are engaged with the endwall 81, at least some spacing is provided between the receiver and male hub (e.g., permitting at least some venting). However, when the engagement members 230 of the fingers 221 are engaged with the endwall 81, the receiver and the male hub are substantially engaged to provide a sealed, interference fit.

Accordingly, by disengaging the two engaged fingers 221 from the connector (e.g., pressing inwardly on each engaged finger to disengage the engagement surface 231 from the endwall 81), the component 100 can be at least partially separated from the connector until the engagement members 230 of the first set of fingers 220 engage with the endwall 81, thereby providing at least some clearance between the interior surface of the receiver of the component and an outer surface of the male hub, thereby providing a vented connection. Thus, according to example embodiments of the present invention, the hub component can be configured for removable engagement with the connector-attaching portion of the vented connector, for example, in either a vented configuration or an interference or sealed configuration depending on which of the fingers 220, 221 are engaged with the endwall 81 of the connector 60.

Figures 7, 8:
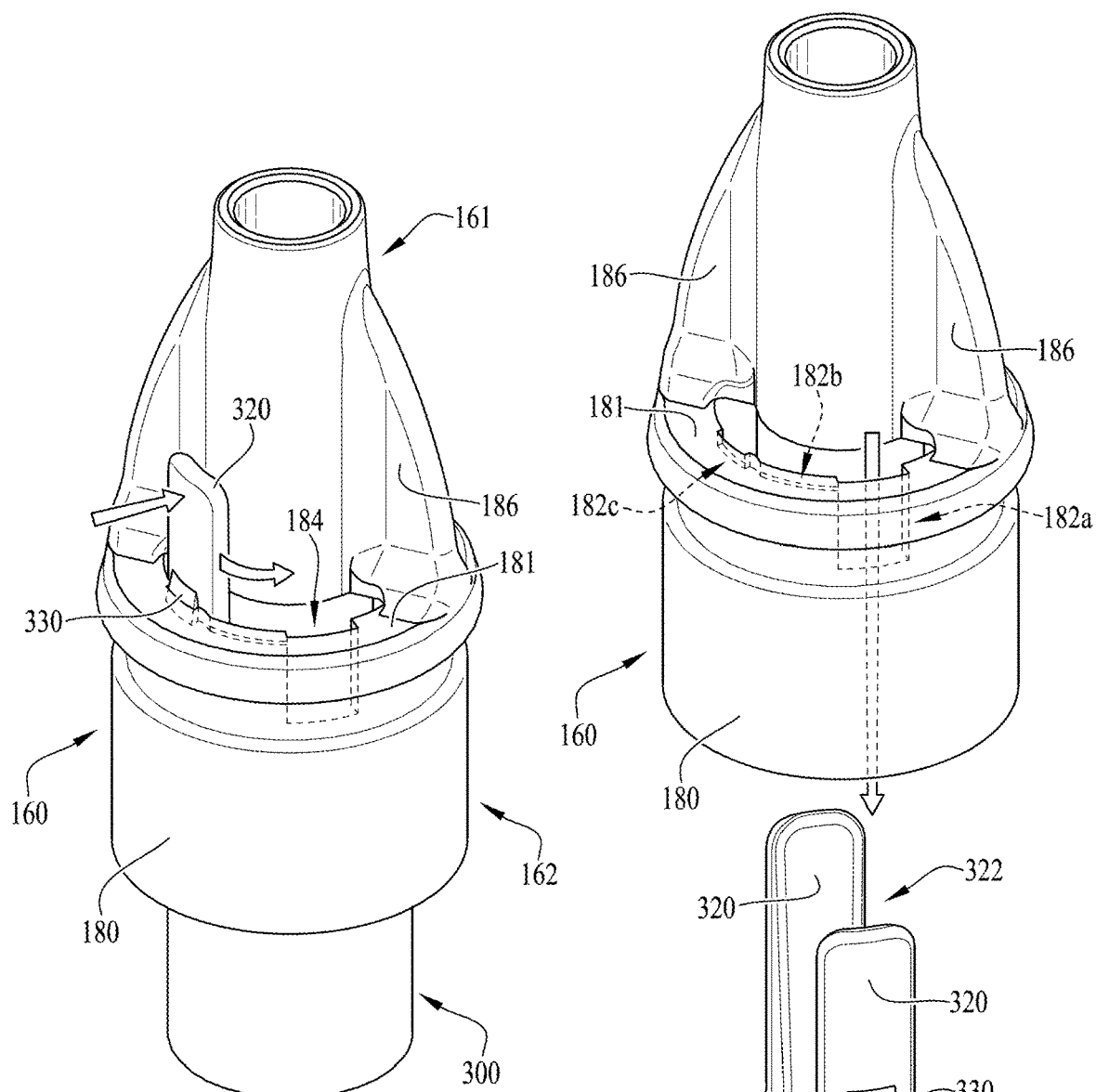
FIG. 7 shows a perspective view of a hub component connected with a vented connector according to another example embodiment of the present invention.
FIG. 8 shows a perspective assembly view of the hub component and vented connector of FIG. 7, wherein the hub component and vented connector are spaced apart and disconnected from each other.

FIGS. 7-8 shows a hub component 300 for compatible engagement with a vented connector 160 according to another example embodiment of the present invention. In example embodiments, the component 300 and connector 160 are preferably removably engageable with each other, for example, similar to a bayonet fitting. In example embodiments, the component 300 is generally similar to the components as described above and comprises a second end comprising a pair of opposing fingers 320 comprising engagement members 330 protruding outwardly therefrom, and wherein a channel 322 is defined between the fingers 320. The connector 160 is generally similar to the connector 60 as described above, however, a channeled engagement track or pathway is provided with the connector 160 so as to permit a rotational/clipped engagement with the fingers 320 of the component 300, for example, which is generally similar to a bayonet fitting.

In example embodiments, the collar 180 comprises the endwall 181 (as described above) and comprises an elongate entrance channel 182a, a radial track 182b extending from the channel 182a, and a coupling recess or catch 182c defined at an end of the radial track 182b. In example embodiments, the component 300 is connected with the connector 160 by moving the fingers through the vents 184 (with the engagement members 330 aligned with the channel 182a), and rotating the component 300 such that the engagement surface 231 of the engagement member 230 rides along the radial track 182b until the engagement member 330 is fitted within the catch 182c. Thereafter, the component 300 is engaged with the connector 160 (and with the receiver providing an interference fit with the male hub). To separate the component 300 from the connector 160, the fingers 320 are pressed or deflected inwardly (see arrow of FIG. 7) until the engagement members 330 are free from engagement with the catch 182c, and then the component 300 is rotated such that the engagement surface 331 rides along the radial track 182b until reaching the channel 182a. The engagement members 330 are then free to pass through the channel 182a thereby permitting full separation of the component 300 from the connector 160. According to some example embodiments, the channel 182a can extend entirely along an internal portion of the collar 180, for example, wherein at least a portion of the threads defined on an internal portion of the collar can be slotted or comprise a groove or recess.

Figure 9:
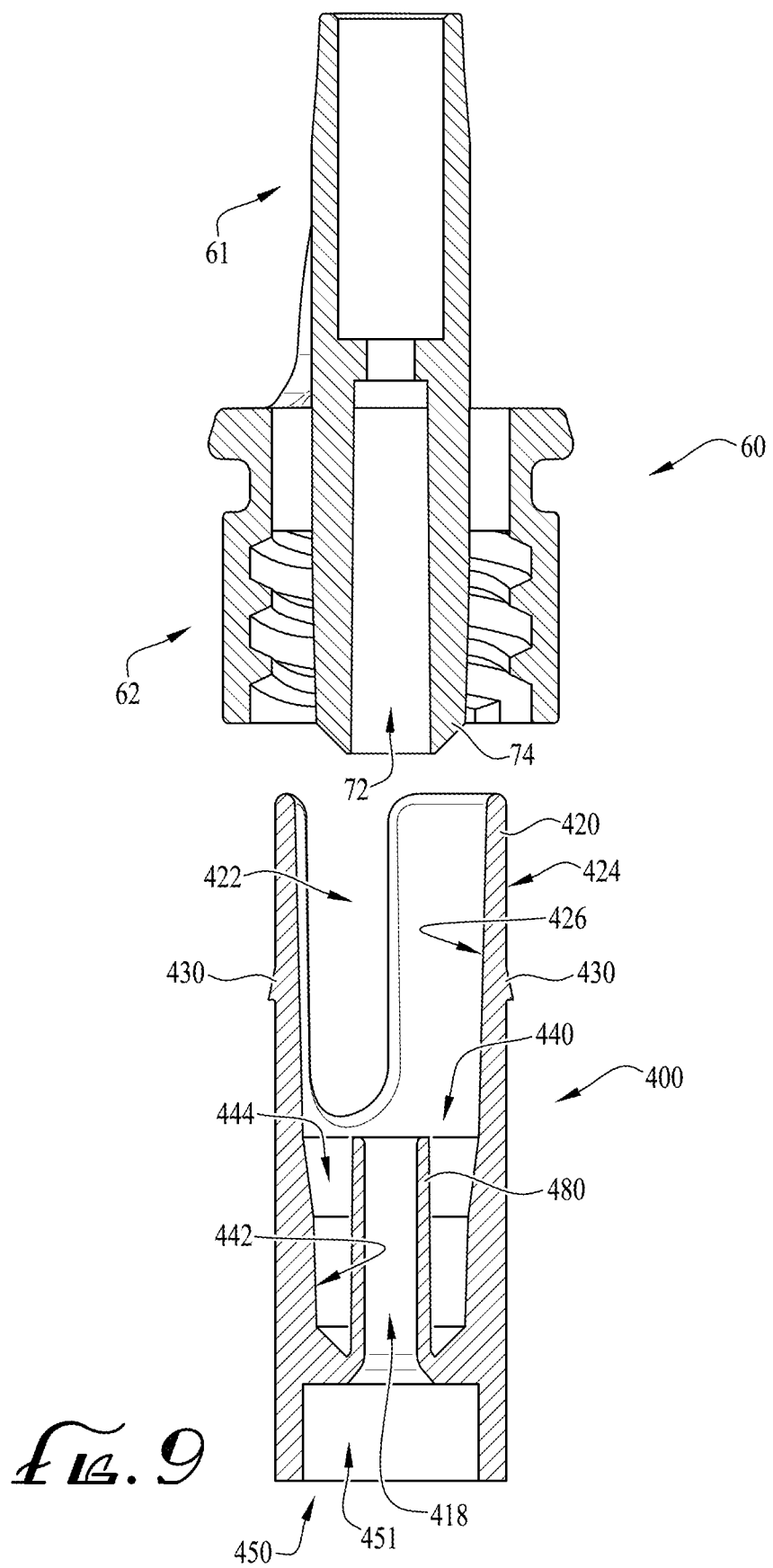
FIG. 9 shows a cross-sectional assembly view of a hub component and a vented connector according to another example embodiment of the present invention.
Figure 10:
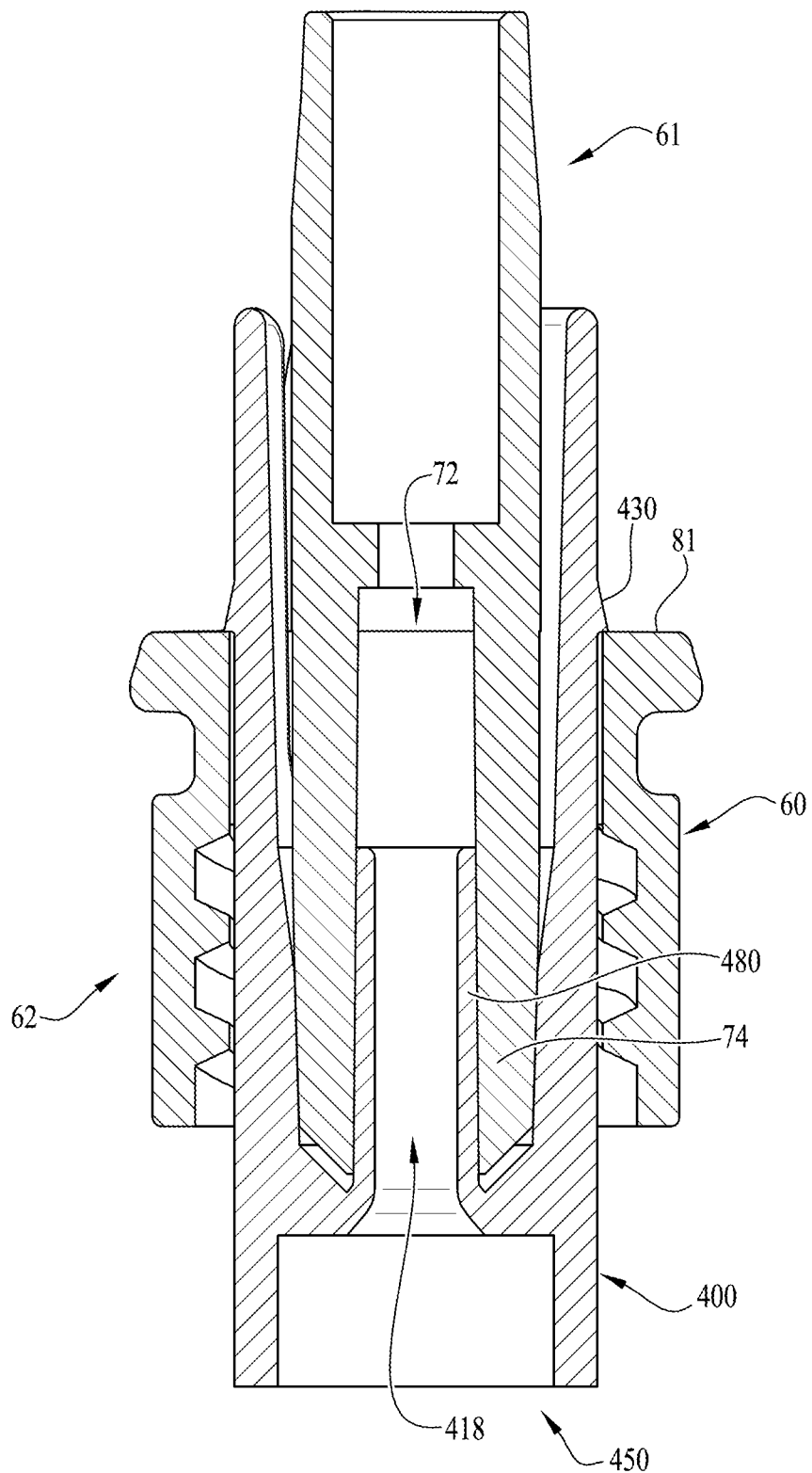
FIG. 10 shows a cross-sectional view of the hub component and vented connector of FIG. 9 connected together.

FIGS. 9-10 show a hub component 400 according to another example embodiment of the present invention. In example embodiments, the component 400 is generally similar to the component 10 as described above. In example embodiments, the receiver 440 further comprises a dosing control coupling or lumen extension tip 480 projecting in a direction generally opposite the coupling portion 450. In example embodiments, with the lumen extension tip 480 projecting therein, an annular space 444 is defined between an inner surface 442 of the receiver an outer or external surface of the lumen extension tip 480. According to example embodiments and shown in FIG. 10, when the component 400 is connected with the connector 60 (with the receiver 40 providing an interference fit with the male hub 74), the lumen extension tip 480 is received within the lumen 72 of the male hub 74. U.S. Published Patent Application US 2016/0317393, Ser. No. 15/210,282 is incorporated herein by reference in its entirety and discloses a dosing control coupling for enteral fluid transfer.

Figure 11:
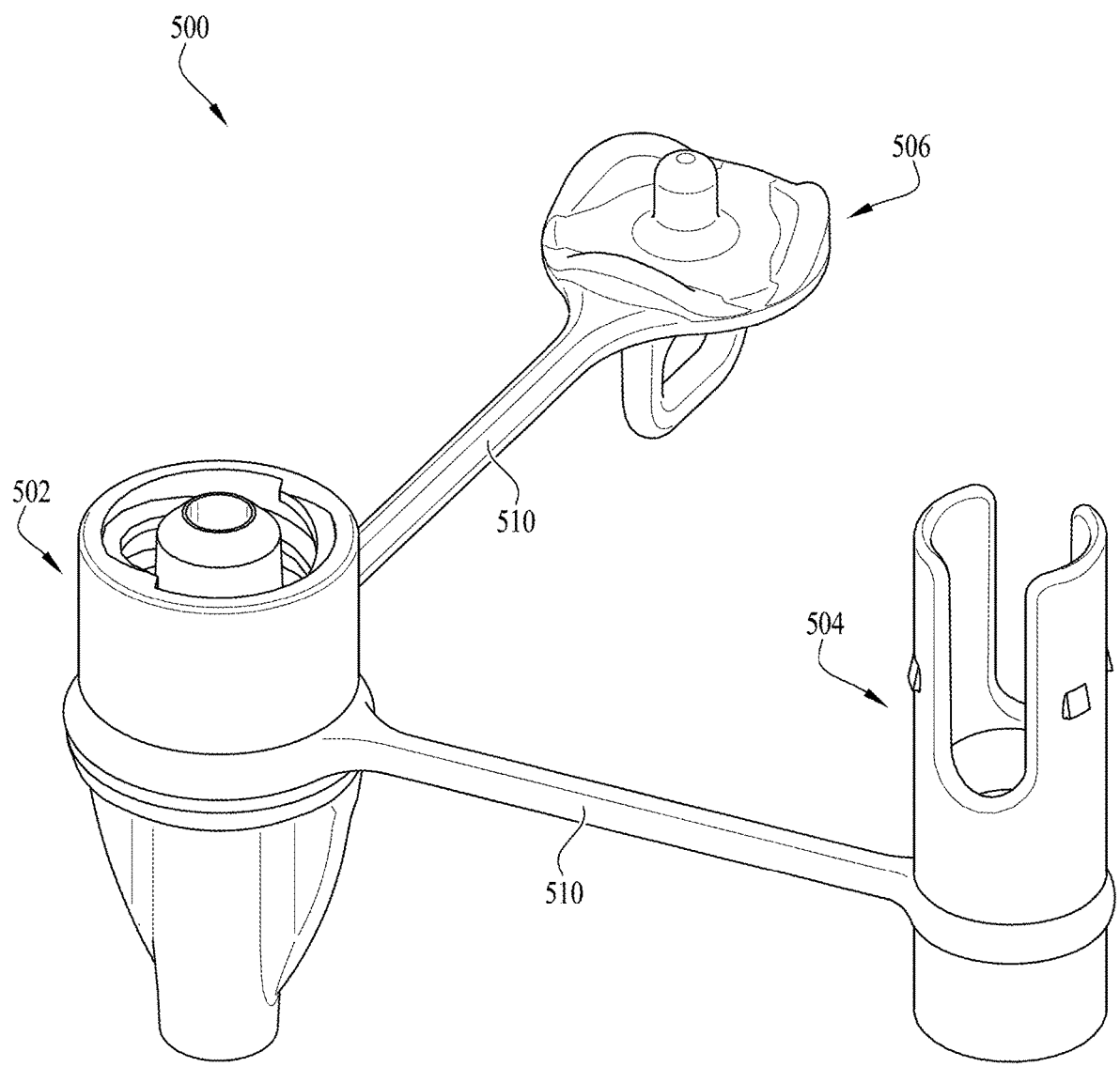
FIG. 11 shows a perspective view of a hub component according to another example embodiment of the present invention, the hub component being tethered to a vented connector and wherein a closure is further tethered to the vented connector.

FIG. 11 shows a connector assembly 500 comprising a vented connector 502, a hub component 504, and a closure or cap 506. In example embodiments, the component 504 and the cap 506 are connected to the connector 502 by a tether or connecting member 510. In use, a user or clinician can readily access either of the component 504 or the cap 506 as desired. According to another example embodiment, one or more additional components, connectors or other closures can be tethered to the connector 502 as desired. According to one example embodiment, the hub component 504 can be connected with the connector 502, and then the cap 506 can be connected to the coupling portion of the component 504, for example, to provide a closure or seal at the coupling portion.

According to one example, a clinician can sealingly engage the hub component to the connector and sealingly engage a $CO_2$ detector to the second end of the hub component to ensure proper gastric placement of the tube or vessel extending from the connector. Additionally, when it is desired to vent the vessel (e.g., after feeding), the hub component can be coupled with the connector in the vented configuration, for example, such that air or gasses are permitted to pass through the vessel, through the lumen of the male coupling, and through the at least partially spaced-apart or offset surfaces of the hub component and male coupling while keeping the male coupling (and lumen thereof) substantially covered and clean or sanitary.

According to some example embodiments, the one or more fingers do not comprise any ribs or surface features, and thus rely on a friction fit with the male coupling of the vented connector. According to another example embodiment, one or more ribs or surface features of the one or more fingers can be configured to provide for a substantially permanent connection, for example, to be used in applications where tamper evidence or re-use prevention is desirable.

While the invention has been described with reference to example embodiments, it will be understood by those skilled in the art that a variety of modifications, additions and deletions are within the scope of the invention, as defined by the following claims.

What is claimed is:

1. A component for coupling engagement with a vented connector comprising one or more vents, the component comprising:
   a cylindrical body extending from a first end to a second end, and a lumen extending through the cylindrical body from the first end to the second end;
   a coupling portion receiver defined at the first end;
   at least one clip defined at the second end; and
   a receiver formed within the cylindrical body between the first and second ends, wherein the receiver comprises an inner surface having a diameter that is tapered from a largest diameter adjacent to the inner surface of each of the at least one clip to a smallest diameter adjacent to the coupling portion receiver;
   wherein the component can be configured for connecting with the vented connector in either of a vented configuration or a sealed configuration;
   wherein in the vented configuration, a first engagement member positioned on an outer surface of the second end at a first height is engaged with an endwall of the vented connector so as to provide at least some space between the inner surface of the receiver and an outer surface of a body of the vented connector;
   wherein in the sealed configuration, a second engagement member positioned on an outer surface of the second end at a second height is engaged with the endwall so as to provide a sealed, interference fit between the inner surface of the receiver and the outer surface of the body of the vented connector; and
   wherein when the at least one clip is passed through the one or more vents, a component-attaching portion of the vented connector is interference fit within the receiver.

2. The component of claim 1, wherein a body of the component-attaching portion comprises a male hub, the male hub being formatted to be compatible with the ISO 80369-3 design standard, and wherein the receiver is formatted to be compatible with the ISO 80369-3 design standard so as to provide complementary interengagement between the component and the vented connector.

3. The component of claim 1, wherein the second engagement member has an engagement surface, the engagement surface configured for interfering with an endwall of a cylindrical collar of the vented connector when the receiver is interference fit with a body of the component-attaching portion.

4. The component of claim 1, wherein the at least one clip comprises a pair of opposing clips defining a pair of elongate channels therebetween.

5. A component, for coupling engagement with a vented connector comprising one or more vents, the component comprising:
   a cylindrical body extending from a first end to a second end, and a lumen extending through the body from the first end to the second end;
   a coupling portion receiver defined at the first end;
   at least one clip defined at the second end; and
   a receiver formed within the cylindrical body between the first and second ends, wherein the receiver comprises an inner surface having a diameter that is tapered from a largest diameter adjacent to the inner surface of each of the at least one clip to a smallest diameter adjacent to the coupling portion receiver;
   wherein when the at least one clip is passed through the one or more vents, a component-attaching portion of the vented connector is interference fit within the receiver;
   wherein the second end of the cylindrical body comprises a first clip and a second clip;
   wherein the first clip comprises a first engagement member formed on an outer surface thereof;
   wherein the second clip comprises a second engagement member formed on an outer surface thereof;
   wherein the first engagement member is positioned at a first height and the second engagement member is positioned at a second height, wherein when the first engagement member engages the vented connector, the receiver of the component and a male hub of the vented connector are in a sealed interference fit; and
   wherein when the second engagement member engages the vented connector, the receiver and the male hub are spaced apart and permit venting thereby.

6. The component of claim 5, wherein the one or more clips are configured for extension through the one or more vents.

7. The component of claim 5, wherein the at least one clip comprises a pair of opposing clips defining a pair of elongate channels therebetween.

8. The component of claim 5, wherein the male hub is formatted to be compatible with the ISO 80369-3 design standard, and wherein the receiver is formatted to be compatible with the ISO 80369-3 design standard so as to provide complementary interengagement between the component and the vented connector.

9. The component of claim 5, wherein the second engagement member has an engagement surface, the engagement surface configured for interfering with an endwall of a cylindrical collar of the vented connector when the receiver is interference fit with a body of the component-attaching portion.

10. A component, for coupling engagement with a vented connector comprising one or more vents, the component comprising:

a cylindrical body extending from a first end to a second end, and a lumen extending through the body from the first end to the second end;

a coupling portion receiver defined at the first end;

at least one clip defined at the second end; and a receiver formed within the cylindrical body between the first and second ends, wherein the receiver comprises an inner surface having a diameter that is tapered from a largest diameter adjacent to the inner surface of each of the at least one clip to a smallest diameter adjacent to the coupling portion receiver;

wherein when the at least one clip is passed through the one or more vents, a component-attaching portion of the vented connector is interference fit within the receiver;

wherein the at least one clip is a circular array of four space-apart clips, wherein at least one of the four clips comprises an engagement member extending from an outer surface thereof; and wherein the four clips include a first pair of clips and a second pair of clips, the first pair of clips comprising a first engagement member formed on an outer surface thereof at a first height and the second pair of clips comprising a second engagement member formed on an outer surface thereof at a second height, wherein the first height is not identical to the second height.

11. The component of claim 10, wherein a body of the component-attaching portion comprises a male hub, the male hub being formatted to be compatible with the ISO 80369-3 design standard, and wherein the receiver is formatted to be compatible with the ISO 80369-3 design standard so as to provide complementary interengagement between the component and the vented connector.

12. The component of claim 10, wherein the second engagement member has an engagement surface, the engagement surface configured for interfering with an end-wall of a cylindrical collar of the vented connector when the receiver is interference fit with a body of the component-attaching portion.

13. The component of claim 10, wherein the at least one clip comprises a pair of opposing clips defining a pair of elongate channels therebetween.

* * * * *